United States Patent [19]

Keenan

[11] Patent Number: 4,536,386
[45] Date of Patent: Aug. 20, 1985

[54] METHOD OF CONTROLLING EMESIS CAUSED BY CISPLATIN IN CANCER CHEMOTHERAPY

[75] Inventor: Robert E. Keenan, Richmond, Va.

[73] Assignee: A. H. Robins Company, Inc., Richmond, Va.

[21] Appl. No.: 508,367

[22] Filed: Jun. 27, 1983

Related U.S. Application Data

[63] Continuation-in-part of Ser. No. 352,728, Feb. 26, 1982, abandoned, which is a continuation-in-part of Ser. No. 228,514, Jan. 26, 1981, abandoned.

[51] Int. Cl.³ .................... A61K 33/24; A61K 31/165
[52] U.S. Cl. ...................................... 424/10; 424/131; 514/619
[58] Field of Search .......................... 424/10, 131, 324

[56] References Cited

U.S. PATENT DOCUMENTS 3,177,252  4/1965  Thomland ........................... 424/324

OTHER PUBLICATIONS

Kahn et al., Cancer Treatment Reports, vol. 62, No. 7, Jul. 1978, pp. 1106–1107.
Gylys, Res. Common in Chem. Path. Pharm. 23(1), pp. 62–68, (1979).

Primary Examiner—Jerome D. Goldberg

[57] ABSTRACT

High dosages of metoclopramide or a pharmaceutical salt thereof is administered intravenously to human cancer patients undergoing cisplatin chemotherapy to prevent emesis.

7 Claims, 1 Drawing Figure

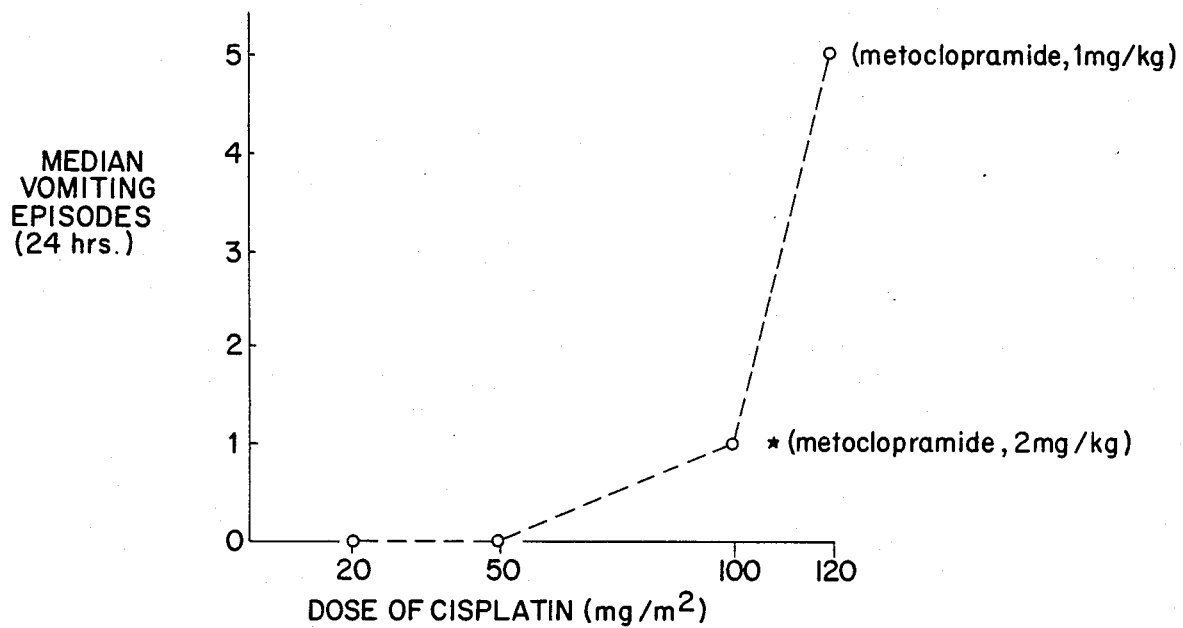

METHOD OF CONTROLLING EMESIS CAUSED BY CISPLATIN IN CANCER CHEMOTHERAPY

The present application is a continuation-in-part application of copending application Ser. No. 352,728 filed Feb. 26, 1982, now abandoned, which is a continuation-in-part application of application Ser. No. 228,514 filed Jan. 26, 1981, now abandoned.

BACKGROUND OF THE INVENTION

1. Field of Invention

Cisplatin (cis-dichlorodiammine platinum II) is one of the more effective drugs used in cancer chemotherapy; however, the resulting violent emesis interferes with acceptance of therapy by the patient. This invention relates to an improvement in the method of alleviating emesis caused by cisplatin with metoclopramide, more specifically with extremely high dosages of metoclopramide administered starting prior to and continuing after cisplatin administration.

2. Information Disclosure Statement

Cisplatin is generally acknowledged to be one of the most emetogenic drugs now available for the chemotherapy of malignant diseases in humans. Though it represents a significant advance in the treatment of human cancer, its use nevertheless provokes vomiting which is particularly violent for several hours in almost all of those to whom it is administered. Patients often refuse further treatment because of its severity. Thus, potentially beneficial effects are jeopardized and effects already achieved are negated by the failure of currently available antiemetics or dosage regimen to consistently relieve or, at the very least to even provide expectancy for reduction in severity and frequency of vomiting.

Standard antiemetics have heretofore been of little value in treating side effects of cisplatin in cancer therapy according to Rosenberg, B. in "Cisplatin, Current Studies and New Developments, "Academic Press, Inc., N. Y., N. Y. pp. 9–20 (1980). Metoclopramide has been used in some diagnostic studies of the gastrointestinal tract in the treatment of vomiting of various etiologies and in a variety of functional and organic gastrointestinal disorders. Results of prior studies on attempts to employ metoclopramide against vomiting caused by cisplatin are somewhat contradictory. Kahn T., et al in Cancer Treatment Report 62 (7): 1106–7 July 1968, reports beneficial antiemetic effect in a single oral dose of two 10 mg metoclopramide tablets per patient 3 hours after administration in patients who had already been treated with combination chemotherapy with several other drugs and cisplatin. In an effort to confirm Kahn's work, Arnold, D. J., et al, reporting in Proc AACR & ASCO 21, 334 (1980) conducted a double-blind study in fifteen patients utilizing 20 mg administration of metoclopramide 30 minutes before and 3 hours after cisplatin administration. The test were terminated because of the lack of effectiveness in significantly ameliorating cisplatin emesis. Higi, M., in Deut. Med. Wochenschr. 105 (22) 794–5 (1980), found metoclopramide, triflupromazine and other phenothiazines all ineffective against platinum induced gastrointestinal toxicity. Gylys, J. A. in Res. Commun. in Chem. Path. Pharm. 23 (1): 62–8 (1979) found metoclopramide (1, 3 mg/kg) subcutaneously administered effective in dogs against cisplatin induced emesis.

The present invention is based on the discovery that control of emesis due to cisplatin administration in humans can be consistently overcome by matching extremely high doses of metoclopramide to high doses of cisplatin. Generally, the higher the dose of cisplatin the higher the dose of metoclopramide needed.

The present invention utilizes from about 10 to about 40 times the total dosage used per treatment in humans by Kahn, et al described above.

SUMMARY OF THE INVENTION

The present invention provides an improved method of utilizing metoclopramide to control emesis in patients receiving cancer chemotherapy with cisplatin. In the method of this invention about 5 to 18 mg metoclopramide per kg body weight of the patient is administered more or less evenly over a period of time of about 30 minutes just prior to cisplatin administration and up to at least 5½ to 13 hours following the cisplatin treatment. Thus, for the average 70 kg human receiving 100 to 120 mg cisplatin per square meter of body surface, a total of about 350 to about 1260 mg metoclopramide or the equivalent of a pharmaceutical salt thereof is administered to each such patient just prior to and in the several hours immediately following the cisplatin treatment.

DETAILED DESCRIPTION OF THE INVENTION

This invention provides an improvement in the treatment of emesis associated with cisplatin chemotherapy for humans suffering from malignant diseases comprised of administering extremely high doses of metoclopramide during a critical phase of the treatment. About 5 to 18 mg metoclopramide per kg of body weight of patient is administered intravenously, orally, peritoneally, intramuscularly, subcutaneously or as suppositories or by a combination of any of these methods. Preferably, about 5 to 18 mg metoclopramide per kg body weight is infused in boluses (15 minute infusions) over a period of time starting about 30 minutes just prior to cisplatin administration and repeated 2 doses at 2 hr intervals and 3 doses at 3 hr intervals.

Metoclopramide which is N-(2-(diethylaminoethyl)-2-methoxy-4-amino-5-chlorobenzamide and preparation thereof is disclosed in U.S. Pat. No. 3,177,252. It or any of the pharmaceutical salts thereof are suitable for the practice of this invention. The monohydrochloride monohydrate salt of metoclopramide 10 mg injectable is on sale as a prescription drug in the United States under the trade name Reglan ®. This salt is preferred in practicing the method of this invention. Tablets, capsules, elixirs, lozenges and suppositories can also be prepared. Multiples of Reglan ® injectables may be used to prepare diluted solutions for intravenous injection in the practice of this invention. Typically, cancer patients are treated repeatedly with cisplatin with variable time intervening between treatments. The carrier for the cisplatin is preferentially a large volume which tends to prevent kidney damage. In the method of this invention, the amount of metoclopramide used is related to the amount of cisplatin administered; e.g., the higher the dose of cisplatin, normally the higher the dose of metoclopramide required to counter the effect but not necessarily in direct proportion (see FIG. 1).

For example, low-dose chemotherapy of cisplatin up to 100 mg/sq. meter of body surface required about 5 mg metoclopramide per kg body weight per treatment per 10–13 hr period. For a higher dose of 120 mg cisplatin/square meter of body surface about 10 mg of metoclopramide/kg of body weight may be required.

At the lower cisplatin dosages up to 100 mg cisplatin/$m^2$ body surface a preferable regiment is to inject intravenously over 15 minute periods (bolus infusion) about 50 ml volumes of solution each containing 1 mg metoclopramide per kg of body weight on the following schedule.

30 minutes prior to cisplatin injection
1½ to 2 hr after cisplatin injection
3½ to 4 hr after cisplatin injection
5½ to 7 hr after cisplatin injection
8½ to 10 hr after cisplatin injection
11½ to 13 hr after cisplatin injection For high dose intravenous chemotherapy of 120 mg cisplatin/$m^2$ body surface the same volume schedule may be used but the metoclopramide content is doubled to 2 mg/kg body weight. Obviously, the intervals between metoclopramide injections may vary somewhat as well as the pretreatment time prior to cisplatin injection and it may be possible to forego the last one to two injections. The metoclopramide solutions may also vary in volume and may be injected as a continuous infusion.

It is preferred that the high doses of metoclopramide be administered intravenously in accordance with the method of this invention. Intravenous administration of the drug may be done conveniently to provide adequate and predictable levels of the drug in the blood of the patient treated.

The following examples illustrate the invention as well as the efficacy of the treatment in humans, but the scope of the invention is not limited thereby.

EXAMPLE 1

Randomized, Double-Blind Study, Antiemetic Effect of Intravenous Metoclopramide Versus Placebo in Patients Receiving Cisplatin The following test was conducted at Memorial Sloan-Kettering Cancer Center in order to accurately assess the antiemetic effect of intravenously administered metoclopramide. A total of 21 patients (17 male, 4 female) were used in the test having a mean age of 53 years with a range from 22 to 74. Eleven patients received chemotherapy for carcinoma of the lung, 8 for esophageal cancer and one each for sarcoma and carcinoma of the larynx. All but 2 patients (placebo group) received Vindesine in combination with cisplatin. Data for all patients (11 metoclopramide, 10 placebo) were suitable for analysis and were followed for an entire 24 hr period.

This was a parallel study in which patients were randomized to receive intravenous metoclopramide (2 mg/kg body weight) or identically appearing placebo (diluent for metoclopramide). The drugs were diluted (from standard drug forms of Reglan ®) in 50 ml of i.v. sodium chloride and given as 15 min infusions 30 minutes prior to cisplatin and 1½, 3½, 5½, 8½ and 11½ hr after cisplatin for a total of 12 mg/kg body weight. All patients were kept NPO on the day of study, prehydrated with 5% dextrose in sodium chloride i.v. and mannitol-induced diuresis by the method of Hayes, D. M. et al in Cancer 39: 1372-8 (1977). Cisplatin (120 mg/$m^2$ body surface was given intravenously over 15 to 20 minutes as part of an approved chemotherapeutic protocol for malignant disease.

Patients who qualified for this study received no prior emesis-producing chemotherapy with stable cardiovascular, hematological, renal and hepatic functions. Patients with known sensitivity to procaine derivatives, and patients experiencing nausea or vomiting for any reason or receiving other antiemetic agents during the 24 hr period proceding administration of cisplatin were excluded from the study.

The total number of vomiting episodes was recorded and each patient's therapeutic response was graded as follows:

Major Response: 0-2 emetic episodes
Minor Response: 3-5 emetic episodes
Equivocal Response: 6-8 emetic episodes
Therapeutic Failure: >8 emetic episodes The volume of emesis was also recorded for each patient.

Results

When metoclopramide was given intravenously at a dose of 2 mg/kg body weight at 30 minutes before and every 2 to 3 hr after administering 120 mg/kg cisplatin for a total of about 12 mg/kg patient body weight, there was a significant reduction in the number of vomiting episodes when compared to identically-treated placebo controls (median of 1 vs 10.5). Thirty-six percent of the metoclopramide group had complete protection from vomiting during the 24 hr period following treatment with cisplatin while all of those who received placebo vomited. In further qualification of treatment, 91% of those treated with metoclopramide had either a major (0-2 episodes) or minor (3-5 episodes) response while 70% of the placebo patients were therapeutic failures (more than 8 episodes). These differences in response were also significant as was the 10-fold reduction in mean volume of emesis (47 cc for metoclopramide vs 557 cc for placebo). Forty-five percent of the metoclopramide patients had no measurable vomiting while the minimum volume for a placebo patient totaled 250 cc.

The most frequently encountered side effect in the tests of Example 1 was sedation which was reported by 82% of the metoclopramide treated patients and 30% of the placebo group. This did not prove troublesome and may be of some benefit to patients who are apprehensive about undergoing chemotherapy. Diarrhea was observed with approximately the same frequency in both treatment groups (73% for metoclopramide and 90% for placebo) which suggests this phenomenon may result from the chemotherapeutic regimen. Other side effects including a single dystonic reaction in a metoclopramide patient were transient and not serious. No patient required termination as a result of adverse effects.

EXAMPLE 2

Antiemetic Effect of Intravenous Metoclopramide (1 mg/kg) Versus Intravenous Metoclopramide (0.25-0.75 mg/kg) in Patients Receiving Cisplatin This was an open-label, multi-investigator study to assess the efficacy and safety of intravenous metoclopramide in patients with malignancy undergoing chemotherapy with cisplatin for the first time; alone or in combination with other anti-neoplastic agents. Patients 18 years or older not previously treated with emesis-inducing chemotherapy were screened and enrolled in the trial. Patients experiencing nausea and vomiting for any reason during the 24 hour period preceding treatment and those known to have psychogenic vomiting as a conditioned reflex were excluded from the study. Pregnant patients or patients with hepatic encephalopathy, uremia, degenerative CNS or extrapyramidal disorders, epilepsy, pheochromocytoms, heart failure or breast cancer were not enrolled. Antiemetics and major tranquilizers were discontinued at least 24 hours prior to starting the trial.

Patients received intravenous metoclopramide (0.25, 0.50, 0.75 or 1 mg/kg). The drug was diluted in 50 ml of i.v. sodium chloride and given as 15 minute infusions 30 minutes prior to cisplatin and 1½, 3½, 6½, 9½ and 12½ hours after cisplatin. All patients were prehydrated with 5% dextrose in sodium chloride i.v. and mannitol-induced diuresis by the method of Hayes, D. M. et et al in Cancer 39: 1372-8 (1977). Cisplatin (20-120 mg/m²) was given intravenously over 15 to 20 minutes as part of an approval chemotherapeutic protocol for malignant disease.

Six patients receiving 20 mg/m² of cisplatin were treated with 0.25-0.75 doses of metoclopramide according to the above schedule. Seventy-five patients receiving 20-120 mg/m² of cisplatin were treated with doses of 1 mg/kg of metoclopramide according to the above schedule. Other antineoplastic agents were allowed without restriction providing their use was adequately documented.

Each patient was hospitalized and observed for the 24 hour period following the initiation of cisplatin. Episodes of vomiting and retching were evaluated and recorded immediately prior to each dose of metoclopramide and at the end of 24 hours. Instances of vomiting separated by a period of less than five minutes were counted as a single episode.

The following tables present the results observed.

| Vomiting episodes | number | percentage |
|---|---|---|
| a. Vomiting Episodes (24 hr.) with Metoclopramide 1 mg/kg (cisplatin 20-120 mg/m²) | | |
| no vomiting | 41* | 54.7% |
| 1-2 | 14 | 18.7% |
| 3-5 | 11 | 14.7% |
| 6-8 | 8 | 10.7% |
| >8 | 1 | 1.3% |
| b. Vomiting Episodes (24 hr.) with Metoclopramide 0.25-0.75 mg/kg (cisplatin 20 mg/m²) | | |
| no vomiting | 0 | 0% |
| 1-2 | 2 | 33.3% |
| 3-5 | 2 | 33.3% |
| 6-8 | 1 | 16.6% |
| >8 | 1 | 16.6% |

*includes 2 patients who did not vomit but experienced continuous nausea/retching.

EXAMPLE 3

Antiemetic Effect of Low Dose Metoclopramide Versus Placebo in Patients Receiving Cisplatin Patients received either 20 mg of metoclopramide or placebo, administered orally, one hour prior to receiving cisplatin and again 3 hours and 9 hours after cisplatin.

The following results were observed

| | Metoclopramide (30 patients) | Placebo (32 patients) |
|---|---|---|
| Number of Emetic Episodes | | |
| Median | 12.0 | 14.0 |
| Range | 4-30 | 8-32 |
| Duration of Nausea (hr.) | | |
| Median | 6.5 | 9.0 |
| Range | 0-19 | 2-18 |
| Duration of Vomiting (hr.) | | |
| Median | 6.0 | 7.0 |
| Range | 2-32 | 4-38 |

Patients receiving low dose metoclopramide exhibited no significant improvement over patients receiving placebo.

EXAMPLE 4

Antiemetic Effect of High Dose Metoclopramide Versus Placebo in Patients Receiving Cisplatin Patients received either high dose intravenous metoclopramide or placebo as follows. Metoclopramide was supplied in 2 ml vials containing 10 mg of the drug. Identical vials containing only the diluent were used as the source of the placebo. The solution containing either metoclopramide (2 mg/kg) or an identical volume of placebo was added to 50 ml of 0.9 percent sodium chloride and infused over 15 minutes at the time of each dose. The dosage was kept constant throughout each trial and was administered at the following times: 30 minutes before cisplatin therapy and 1½; 3½; 5½ and 8½ hours after therapy. The following results were observed:

| | Metoclopramide (11 patients) | Placebo (10 patients) |
|---|---|---|
| Number of Emetic Episodes | | |
| Median | 1 | 10.5 |
| Range | 0-9 | 5-25 |
| Volume of Emesis (ml.) | | |
| Median | 20 | 404 |
| Range | 0-225 | 250-1870 |
| Duration of Nausea (hr.) | | |
| Median | 0 | 3.7 |
| Range | 0-16.2 | 0-19.2 |
| Duration of Vomiting (hr) | | |
| Median | 0.2 | 3.6 |
| Range | 0-16.8 | 2-17.0 |

Patients treated with metoclopramide had significantly fewer episodes of vomiting and significantly less volume of emesis than patients treated with placebo. The durations of nausea and vomiting were significantly shorter in patients receiving metoclopramide than in those given placebo.

EXAMPLE 5

Antiemetic Effect of Metoclopramide versus Prochlorperazine in Patients Receiving Cisplatin Patients received either intravenous metoclopramide or intramuscular prochlorperazine with all patients being given both intravenous and intramuscular doses at the time of each administration. The doses and schedules of metoclopramide and intravenous placebo were the same as given in Example 4. Patients randomly assigned to receive prochlorperazine in this parallel study were given 10 mg of the drug intramuscularly at the start of each intravenous placebo administration. Patients randomly assigned to receive metoclopramide in this study were given an intramuscular placebo (2 ml of 0.9 percent sodium chloride) identical in appearance and in volume to the prochlorperazine injection at the start of each metoclopramide dosage. The following results were observed:

|  | Metoclopramide (10 patients) | Prochlorperazine (10 patients) |
| --- | --- | --- |
| Number of Emetic Episodes | | |
| Median | 1.5 | 12 |
| Range | 0–6 | 5–6 |
| Volume of Emesis (ml) | | |
| Median | 15 | 208 |
| Range | 0–300 | 16–755 |
| Duration of Nausea (hr) | | |
| Median | 0.1 | 5.0 |
| Range | 0–17.2 | 0–20 |
| Duration of Vomiting (hr) | | |
| Median | 0.5 | 4.5 |
| Range | 0–16.5 | 1.5–17.6 |

Patients receiving metoclopramide had significantly fewer episodes of vomiting than patients receiving prochlorperazine. Metoclopramide was significantly more effective in decreasing the volume of emesis than prochlorperazine. Duration of nausea and vomiting were reduced by metoclopramide in comparison to prochlorperazine. In addition, metoclopramide was well tolerated by patients, with no serious side effects. Sedation was the most frequent side effect seen, occurring in 76 percent of patients given metoclopramide.

EXAMPLE 6

Antiemetic Effect of Intravenous Metoclopramide at 1 mg/kg/dose ×2 doses versus Intravenous Metoclopramide at 1 mg/kg/dose ×6 doses in Patients Receiving Cisplatin This was an open-label, multi-investigator study to assess the efficacy and safety of intravenous metoclopramide in patients with malignancy undergoing chemotherapy with cisplatin for the first time; alone or in combination with other anti-neoplastic agents. Patients 18 years or older not previously treated with emesis-inducing chemotherapy were screened and enrolled in the trial. Patients experiencing nausea and vomiting for any reason during the 24 hour period preceding treatment and those known to have psychogenic vomiting as a conditioned reflex were excluded from the study. Pregnant patients or patients with hepatic encephalopathy, uremia, degenerative CNS or extrapyramidal disorders, epilepsy, phenochromocytoma, heart failure or breast cancer were not enrolled. Antiemetics and major tranquilizers were discontinued at least 24 hours prior to starting the trial.

Patients received intravenous metoclopramide on two schedules (1 mg/kg/dose ×2 doses at 30 minutes prior to and 90 minutes after the onset of chemotherapy or 1 mg/kg/dose ×6 doses at 30 minutes before and $1\frac{1}{2}$, $3\frac{1}{2}$, $5\frac{1}{2}$, $8\frac{1}{2}$ and $11\frac{1}{2}$ hours after chemotherapy. The drug was diluted in 50 ml of i.v. sodium chloride and given as 15 minute infusions. All patients were prehydrated with 5% dextrose in sodium chloride i.v. and mannitol-induced diuresis by the method of Hayes, D. M. et al in Cancer 39: 1372–8 (1977). Cisplatin (20–120 mg/m$^2$) was given intravenously over 15 to 20 minutes as part of an approval chemotherapeutic protocol for malignant disease.

Three patients receiving 120 mg/m$^2$ of cisplatin were treated with 2 doses of 1 mg/kg/dose of metoclopramide according to the above schedule. Ten patients receiving 120 mg/m$^2$ of cisplatin were treated with 6 doses of 1 mg/kg/dose of metoclopramide according to the above schedule. Other antineoplastic agents were allowed without restriction providing their use was adequately documented.

Each patient was hospitalized and observed for the 24 hour period following the initiation of cisplatin. Eposides of vomiting and retching were evaluated and recorded immediately prior to each dose of metoclopramide and at the end of 24 hours. Instances of vomiting separated by a period of less than five minutes were counted as a single episode.

The following results were observed:
Mean number of vomiting episodes observed with 1 mg/kg/dose ×2 dose regimen: 8
Mean number of vomiting episodes observed with the 1 mg/kg/dose ×5–6 dose regimen: 0

EXAMPLE 7

Antiemetic Effect of Intravenous Metoclopramide at 3 mg/kg/dose ×2 doses versus Intravenous Metoclopramide at 3 mg/kg/dose ×4–5 doses in Patients Receiving Cisplatin This was an open-label, multi-investigator study to assess the efficacy and safety of intravenous metoclopramide in patients with milignancy undergoing chemotherapy with cisplatin for the first time; alone or in combination with other anti-neoplastic agents. Patients 18 years or older not previously treated with emesis-inducing chemotherapy were screened and enrolled in the trial. Patients experiencing nausea and vomiting for any reason during the 24 hour period preceding treatment and those known to have psychogenic vomiting as a conditioned reflex were excluded from the study. Pregnant patients or patients with hepatic encephalopathy, urenia, degenerative CNS or extrapyramidal disorders, epilepsy, pheochromocytoma, heart failure, or breast cancer were not enrolled. Antiemetics and major tranquilizers were discontinued at least 24 hours prior to starting the trial.

Patients received intravenous metoclopramide in three schedules (3 mg/kg/dose×2 doses at 30 minutes prior to and 90 minutes after the onset of chemotherapy; 3 mg/kg/dose×4 doses at 30 minutes before and $1\frac{1}{2}$, $3\frac{1}{2}$ and $5\frac{1}{2}$ hours after chemotherapy; and 3 mg/kg/dose×5 doses at 30 minutes before and $1\frac{1}{2}$, $3\frac{1}{2}$, $5\frac{1}{2}$ and $8\frac{1}{2}$ hours after chemotherapy). The drug was diluted in 50 ml of i.v. sodium chloride and given as 15 minute infusions. All patients were prehydrated with 5% dextrose in sodium chloride i.v. and mannitol-induced diuresis by the method of Hayes, D. M. et al in Cancer 39: 1372—8 (1977). Cisplatin (120 mg/m$^2$) was given intravenously over 15 to 20 minutes as part of an approval chemotherapeutic protocol for malignant disease.

Nine patients receiving 120 mg/m$^2$ of cisplatin were treated with 2 doses of metoclopramide according to the above schedule. Five patients receiving 120 mg/m$^2$ of cisplatin were treated with 4 doses of 3 mg/kg/dose of metoclopramide according to the above schedule and five patients receiving 120 mg/m$^2$ of cisplatin were treated with 5 doses of 3 mg/kg/dose of metoclopramide according to the above schedule. Other antineoplastic agents were allowed without restriction providing their use was adequately documented.

Each patient was hospitalized and observed for the 24 hour period following the initiation of cisplatin. Episodes of vomiting and retching were evaluated and recorded immediately prior to each dose of metoclopramide and at the end of 24 hours. Instances of vomiting separated by a period of less than five minutes were counted as a single episode.

The following results were observed:

Mean number of vomiting episodes observed with the 3 mg/kg/dose×2 dose regimen: 8

Mean number of vomiting episodes observed with the 3 mg/kg/dose×4 dose regimen: 2

Mean number of vomiting episodes observed with the 3 mg/kg/dose×5 dose regimen: 1

Formulation and Administration

The pharmaceutical compositions of this invention are comprised of metoclopramide or a pharmaceutical salt thereof and a carrier therefor. The pharmaceutical carrier employed in the composition can be either solid or liquid. When the compositions are administered orally, solid carriers are chosen from such as lactose, magnesium or aluminum stearate, terra alba, sucrose, talc, stearic acid, gelatin, agar, and pectin acacia. Exemplary of carriers for oral administration are vegetable oils and water. When route of administration is oral, parenteral, intravenous or intramuscular, water is an ideal carrier.

A wide variety of pharmaceutical forms can be employed by methods well known to the art. Thus, if a solid carrier is used, the composition can be tableted or prepared as a powder, a trouche, a lozenge, or a suppository. Gelatin capsules containing the medicament can also be prepared. If an oral liquid carrier is used, the composition can be in the form of a soft gelatin capsule, a liquid suspension, or a syrup. Parenteral dosage forms are obtained by dissolving a water-soluble salt of metoclopramide in water or saline solution. The solution can then be filled into single or multiple dose ampoules.

A suitable carrier for the intravenous-injectable is a soluble form of metoclopramide prepared by adding an aqueous solution of preferably metoclopramide hydrochloride monohydrate to solutions containing water, sodium chloride and sodium metabisulfite to a parenteral solution selected from such as Dextrose $-5\%$ in water, Sodium Chloride Injection; Dextrose $-5\%$ in 0.45% sodium chloride, Ringer's Injection and Lactated Ringer's Injection. Dilutions should be protected fron light after preparation. Injectable metoclopramide such as the above should not be prepared more than one hour prior to use.

As stated above, each injection of metoclopramide may be in the form of a 50 ml volume of injectable liquid. Each injection solution should contain a quantity of metoclopramide commensurate with the amount of cisplatin used according to the outline above and provision should be made for preparing fresh solutions for the subsequent injection. As stated above, the metoclopramide solutions are then administered intravenously as 15 minute infusions at spaced intervals, one prior to and 4, 5 or more fllowing cisplatin infusion at approximately $1\frac{1}{2}$ to 3 hr intervals or as continuous infusion. If desired, maintenance dosages of metoclopramide may be given orally, subcutaneously or intramuscularly following the foregoing more intensive regimen.

What is claimed is:

1. A method for alleviating emesis in human cancer patients caused by cisplatin chemotherapy which comprises administering about 5 to 18 mg of metoclopramide or a pharmaceutically acceptable salt thereof per kg of patient body weight over a period of time spanning about 30 minutes prior to cisplatin administration through the post administration period, said metoclopramide or the pharmaceutically acceptable salt thereof being administered either continuously or as 4 to 7 individually spaced dosages about $1\frac{1}{2}$ to 3 hours apart.

2. The method of claim 1 wherein the metoclopramide or a pharmaceutically acceptable salt thereof is administered intraveneously in the presence of a liquid carrier therefor.

3. The method of claim 1 wherein the metoclopramide or a pharmaceutically acceptable salt thereof is divided into 4 to 7 individually spaced dosages which are administered about $1\frac{1}{2}$ to 3 hours apart.

4. The method of claim 3 wherein the amount of cisplatin administered is about 100 mg/square meter or less of patient body surface and each of the individually spaced dosages are comprised of about 1 mg contained metoclopramide per kg of body weight.

5. The method of claim 3 wherein the amount of cisplatin administered is at or above about 120 mg/square meter of patient body surface and each of the individually spaced dosages are comprised of about 2-3 mg contained metoclopramide per kg of body weight.

6. The method of claim 1 wherein the monohydrochloride monohydrate salt of metoclopramide is used 7. The method of claim 1 wherein the metoclopramide or a pharmaceutically acceptable salt thereof is administered as a continuous infusion.

* * * * *

US004536386B1

REEXAMINATION CERTIFICATE (2497th)

United States Patent [19]
Keenan

[11] B1 4,536,386

[45] Certificate Issued Mar. 7, 1995

[54] METHOD OF CONTROLLING EMESIS CAUSED BY CISPLATIN IN CANCER CHEMOTHERAPY

[75] Inventor: Robert E. Keenan, Richmond, Va.

[73] Assignee: A. H. Robins Company, Inc., Richmond, Va.

Reexamination Request:
No. 90/001,397, Dec. 18, 1987

Reexamination Certificate for:
Patent No.: 4,536,386
Issued: Aug. 20, 1985
Appl. No.: 508,367
Filed: Jun. 27, 1983

Related U.S. Application Data

[63] Continuation-in-part of Ser. No. 352,728, Feb. 26, 1982, abandoned, which is a continuation-in-part of Ser. No. 228,514, Jan. 26, 1981, abandoned.

[51] Int. Cl.$^6$ .................. A61K 49/00; A61K 33/24; A61K 31/165
[52] U.S. Cl. .................. 424/10; 424/649; 514/619
[58] Field of Search ............................ 424/10

[56] References Cited

U.S. PATENT DOCUMENTS
5,081,153  1/1992  Pathak et al. .................. 514/619

OTHER PUBLICATIONS

Gralla I (Gralla, Richard J. et al., Antiemetic Efficacy of High–Dose Metoclopramide: Randomized Trials With Placebo and Prochlorperazine In Patients With Chemotherpay-Induced Nausea and Vomiting, N.E.J. of Med. 305:905–909 (Oct. 15, 1981)).

Gralla II (Gralla, Richard J. et al., Phase I Intravenous Trial Of The Antiemetic Metoclopramide In Patients Receiving Cis–Platinum (DDP), Asco Abstracts, C–122 (1980)).

Poster (Poster, Don S. et al., Treatment of Cancer Chemotherapy–Induced Nausea and Vomiting, NCI, Div. of Cancer Treatment, Cancer Therapy Eval. Program (1981).

Smith (Smith, Marie A. et al, New Drug Evaluations, Metoclopramide, Drug Intelligence and Clinical Pharmacy, vol. 14 (Mar. 1980).

Kahn (Kahn et al, Cancer Treatment Reports, vol. 62, No. 7, pp. 1106–1107 (Jul. 1978)).

Gylys (Gylys, J. A., Res. Commun. in Chem. Path. Pharm. 23 (1):62–8 (1979)).

*Primary Examiner*—Jerome J. Goldberg

[57] ABSTRACT

High dosages of metoclopramide or a pharmaceutical salt thereof is administered intravenously to human cancer patients undergoing cisplatin chemotherapy to prevent emesis.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, lines 28, through Column 9 line 10:

[EXAMPLE 6

Antiemetic Effect of Intravenous Metoclopramide at 1 mg/kg/dos×2 doses versus Intravenous Metroclopramide at 1 mg/kg/dose×6 doses in Patients Receiving Cisplatin This was an open-label, multi-investigator study to assess the efficacy and safety of intravenous metoclopramide in patients with malignancy undergoing chemotherapy with cisplatin for the first time; alone or in combination with other anti-neoplastic agents. Patients 18 years or older not previously treated with emesis-inducing chemotherapy were screened and enrolled in the trial. Patients experiencing nausea and vomiting for any reason during the 24 hour period preceding treatment and those known to have psychogenic vomiting as a conditioned reflex were excluded from the study. Pregnant patients or patients with hepatic encephalopathy, uremia, degenerative CNS or extrapyramidal disorders, epilepsy, phenochromocytoma, heart failure or breast cancer were not enrolled. Antiemetics and major tranquilizers were discontinued at least 24 hours prior to starting the trial.

Patients received intravenous metoclopramide on two schedules (1 mg/kg/dose×2 doses at 30 minutes prior to and 90 minutes after the onset of chemotherapy or 1 mg/kg/dose×6 doses at 30 minutes before and 1½, 3½, 5½, 8½ and 11½ hours after chemotherapy. The drug was diluted in 50 ml of i.v. sodium chloride and given as 15 minutes infusions. All patients were prehydrated with 5% dextrose in sodium chloride i.v. and mannitol-induced diuresis by the method of Hayes, D. M. et al in Cancer 39: 1372-8 (1977). Cisplatin (20–120 mg/m$^2$) was given intravenously over 15 to 20 minutes as part of an approval chemotherapeutic protocol for malignant disease.

Three patients receiving 120 mg/m$^2$ of cisplatin were treated with 2 doses of 1 mg/kg/dose of metoclopramide according to the above schedule. Ten patients receiving 120 mg/m$^2$ of cisplatin were treated with 6 doses of 1 mg/kg/dose of metoclopramide according to the above schedule. Other antineoplastic agents were allowed without restriction providing their use was adequately documented.

Each patient was hospitalized and observed for the 24 hour period following the initiation of cisplatin. Eposides of vomiting and retching were evaluated and recorded immediately prior to each dose of metoclopramide and at the end of 24 hours. Instances of vomiting separated by a period of less than five minutes were counted as a single episode.

The following results were observed:
Mean number of vomiting episodes observed with 1 mg/kg/dose×2 dose regimen: 8
Mean number of vomiting episodes observed with the 1 mg/kg/dose×5–6 dose regimen: 0

EXAMPLE 7

Antiemetic Effect of Intravenous Metoclopramide at 3 mg/kg/dose×2 doses versus Intravenous Metoclopramide at 3 mg/kg/dose×4–5 doses in Patients Receivign Cisplatin This was an open-label, multi-investigator study to assess the efficacy and safety of intravenous metoclopramide in patients with malignancy undergoing chemotherapy with cisplatin for the first time; alone or in combination with other anti-neoplastic agents. Patients 18 years or older not previously treated with emesis-inducing chemotherapy were screened and enrolled in the trial. Patients experiencing nausea and vomiting for any reason during the 24 hour period preceding treatment and those known to have pyschogenic vomiting as a conditioned reflex were excluded from the study. Pregnant patients or patients with hepatic encephalopathy, urenia, degenerative CNS or extrapyramidal disorders, epilepsy, pheochromocytoma, heart failure, or breast cancer were not enrolled. Antiemetics and major tranquilizers were discontinued at least 24 hours prior to starting the trail.

Patients received intravenous metoclopramide in three schedules (3 mg/kg/dose×2 doses at 30 minutes prior to and 90 minutes after the onset of chemotherapy; 3 mg/kg/dose×4 doses at 30 minutes before and 1½, 3½ and 5½ hours after chemotherapy; and 3 mg/kg/dose×5 doses at 30 minutes before and 1½, 3½, 5½ and 8½ hours after chemotherapy). The drug was diluted in 50 ml of i.v. sodium chloride and given as 15 minute infusions. All patients were prehydrated with 5% dextrose in sodium chloride i.v. and mannitol-induced diuresis by the method of Hayes, D. M. et al in Cancer 39: 1372—8 (1977). Cisplatin (120 mg/m$^2$) was given intravenously over 15 to 20 minutes as part of an approval chemotherapeutic protocol for malignant disease.

Nine patients receiving 120 mg/m$^2$ of cisplatin were treated with 2 doses of metoclopramide according to the above schedule. Five patients receiving 120 mg/m$^2$ of cisplatin were treated with 4 doses of 3 mg/kg/dose of metoclopramide according to the above schedule and five patients receiving 120 mg/m$^2$ of cisplatin were treated with 5 doses of 3 mg/kg/dose of metoclopramide according to the above schedule. Other antineoplastic agents were allowed without restriction providing their use was adequately documented.

Each patient was hospitalized and observed for the 24 hour period following the initiation of cisplatin. Episodes of vomiting and retching were evaluated and recorded immediately prior to each dose of metoclopramideand at the end of 24 hours. Instances of vomiting separated by a period of less than five minutes were counted as a single episode.

The following results were observed:
Mean number of vomiting episodes observed with the 3 mg/kg/dose×2 dose regimen: 8
Mean number of vomiting episodes observed with the 3 mg/kg/dose×4 dose regimen: 2

Mean number of vomiting episodes observed with the 3 mg/kg/dose×5 dose regimen: 1

AS A RESULT OF REEXAMINATION, IT HAS BEEN DETERMINED THAT:

Claims 1 and 3 are determined to be patentable as amended.

Claims 2, 4, 5 and 6 dependent on an amended claim, are determined to be patentable.

1. A method for alleviating emesis in human cancer patients caused by cisplatin chemotherapy which comprises administering about 5 to 18 mg of metoclopramide or a pharmaceutically acceptable salt thereof per kg of patient body weight over a period of time spanning about 30 minutes prior to cisplatin administration through the post administration period, said metoclopramide or the pharmaceutically acceptable salt thereof being administered either continuously or as [4] 5 to 7 individually spaced dosages about 1½ to 3 hours apart.

3. The method of claim 1 wherein the metoclopramide or a pharmaceutically acceptable salt thereof is divided into [4] 5 to 7 individually spaced dosages which are administered about 1½ to 3 hours apart.

* * * * *